United States Patent [19]
Malmgren

[11] Patent Number: 5,738,270
[45] Date of Patent: Apr. 14, 1998

[54] BRAZELESS CERAMIC-TO-METAL BONDING FOR USE IN IMPLANTABLE DEVICES

[75] Inventor: Richard P. Malmgren, Castaic, Calif.

[73] Assignee: Advanced Bionics Corporation, Sylmar, Calif.

[21] Appl. No.: 625,513

[22] Filed: Mar. 25, 1996

Related U.S. Application Data

[63] Continuation-in-part of Ser. No. 319,580, Oct. 7, 1994, Pat. No. 5,513,793.

[51] Int. Cl.⁶ .................................................. B23K 20/00
[52] U.S. Cl. ............................... 228/193; 228/124.6
[58] Field of Search ............................ 228/190, 193, 228/195, 212, 124.6, 262.21, 262.71

[56] References Cited

U.S. PATENT DOCUMENTS

| Re. 33,859 | 3/1992 | Gurol | 428/76 |
|---|---|---|---|
| 3,784,726 | 1/1974 | Smith et al. | 257/699 |
| 3,786,559 | 1/1974 | Smith | 228/193 |
| 4,041,955 | 8/1977 | Kelly et al. | 128/419 P |
| 4,159,075 | 6/1979 | Ljung et al. | 228/116 |
| 4,525,766 | 6/1985 | Petersen | 361/283 |
| 4,618,802 | 10/1986 | Schrank | 313/512 |
| 4,627,958 | 12/1986 | Hays | 419/8 |
| 4,693,409 | 9/1987 | Mizunoya et al. | 228/262.21 |
| 4,725,480 | 2/1988 | Gurol | 428/210 |
| 4,729,504 | 3/1988 | Edamura | 228/262.72 |
| 4,861,641 | 8/1989 | Foster et al. | 428/137 |
| 4,882,298 | 11/1989 | Moeller et al. | 437/212 |
| 4,906,311 | 3/1990 | Gurol | 156/89 |
| 4,991,582 | 2/1991 | Byers et al. | 128/419 P |
| 5,181,647 | 1/1993 | Runyan | 228/44.3 |

FOREIGN PATENT DOCUMENTS 9408539  4/1994  WIPO.

*Primary Examiner*—Samuel M. Heinrich
*Attorney, Agent, or Firm*—Fitch, Even, Tabin & Flannery

[57] ABSTRACT

In method of forming a hermetically sealed electrical feedthrough comprising, a feedthrough is positioned in a hole, the hole passing through a structure. The feedthrough includes a first material and the structure including a second material. A compressive force directed at the structure is applied to the feedthrough, and an equal force directed at the feedthrough is applied to the structure. The equal force is applied in a direction opposite the compressive force. The feedthrough and the structure are heated to a diffusion temperature whereat the first material and the second material undergo diffusion so as to cause a hermetically sealed bond between the first and second materials, and the hermetically sealed bond is thereby formed between the feedthrough and the structure.

19 Claims, 4 Drawing Sheets

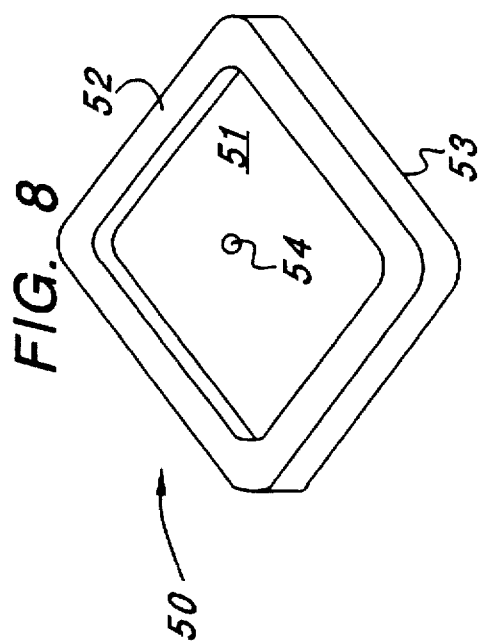
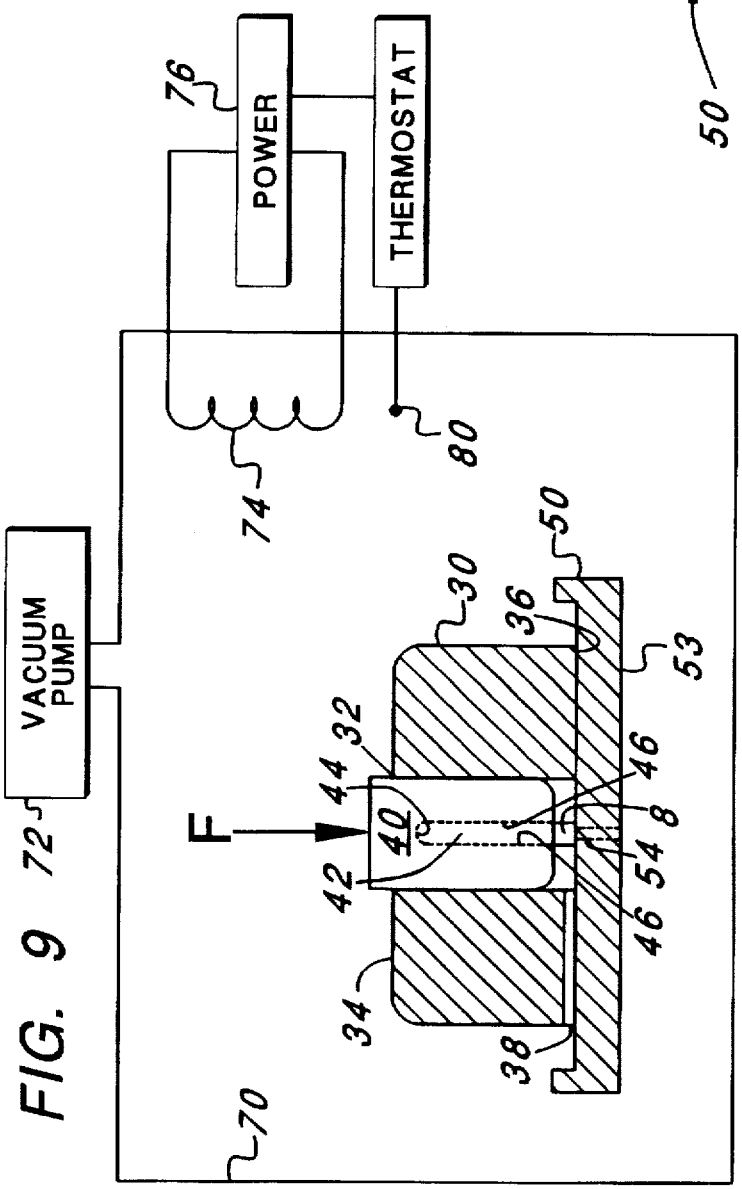

BRAZELESS CERAMIC-TO-METAL BONDING FOR USE IN IMPLANTABLE DEVICES

This application is a Continuation-In-Part of Ser. No. 08/319,580, entitled BRAZELESS CERAMIC-TO-METAL BOND FOR USE IN IMPLANTABLE DEVICES; Filed Oct. 7, 1994, now U.S. Pat. No. 5,513,793.

BACKGROUND OF THE INVENTION

The present invention relates to bonding of materials, and more particularly to brazeless bonding of dissimilar materials. Even more particularly, the present invention relates to brazeless hermetically sealed bonding of ceramic to metal for use in implantable devices.

Stimulators that are to be implanted in living bodies and powered from external informational sources must be housed in packages of biocompatible material. Such packages must protect the electronic circuitry within the implanted stimulator from body fluids and ions so that the circuitry can survive for extended periods without any significant changes in performance.

Today, the most commonly used metals for implantable packages are titanium, stainless steel and cobalt-chromium alloys. These metals are biocompatible and corrosion resistant. Normally, the package consists of two parts welded together to insure hermeticity. The electrical components inside the package are connected to stimulating leads by hermetic feedthroughs, which permit the flow of electrical currents through the package while maintaining hermeticity. However, where there is a need to inductively couple an alternating electromagnetic field to an internal pickup coil, the metal package becomes a hindrance. Specifically, transmission of power is substantially reduced by eddy currents generated in the metal package due to the alternating electromagnetic field. To solve that problem, receiving coils are often placed outside the metal package, increasing the size and complexity of the of the implanted device.

It is known that the glasses and ceramics are transparent to alternating electromagnetic fields and that receiving antennas can be placed inside a hermetic zone of a ceramic or glass package, creating an overall smaller and simpler implant device and reducing the possibility of antenna failure due to saline leakage. Glasses and ceramics are inert and highly insoluble, which are favorable characteristics for long term implant materials. Unfortunately, however, because glasses and ceramics are inelastic, they are subject to fracture not only from mechanical shock but also from differential thermal expansion if even a moderate temperature gradient exists thereacross. Therefore, welding is not a practical method of sealing glass or ceramic materials. Instead, virtually the entire package and its contents must be raised to the melting temperature of the glass, ceramic or metal braze used to effect a sealing of the glass or ceramic package. Such sealing methods are unsatisfactory.

All known biocompatible glasses and ceramics are characterized by high sealing temperatures that will damage electronic components commonly included in electronic devices implanted in living bodies. Low melting temperature glasses all have the property of being corroded by body fluids. Further, metal or glass frits and solders useful in brazing glasses and ceramics and having melting temperatures below the thermal damage limits of implanted electronic components are either not biocompatible or corrode easily in body solutions. Therefore, packages composed entirely of ceramic and/or glass are not considered practical for such implant applications.

Also, in many ceramic and glass packages, the metal solder used to seal the main body and cap portions thereof forms a closed loop that is very close to coaxial with, or in a plane parallel to, the receiving coil used as the antenna for the electronics housed in the implantable package. Thus configured, the closed metal loop or solder acts as a shunt to the alternating electromagnetic fields impressed upon the package to transmit power and/or data to the implanted electronics. This has resulted in the generation of undesired heat within the package and the reduction of power transfer efficiency.

A packaged combination of one ceramic and two metal members is shown in U.S. Pat. No. 4,991,582, issued to Byers et al. and incorporated herein by reference. The one ceramic member is a ceramic case and one of the metal members is a metal band. The other metal member is a header plate. The ceramic case and the metal band are hermetically sealed together, each being characterized by similar coefficients of linear thermal expansion. The final package closure is effected by soldering the metal band to the ceramic case and the metal header plate to the metal band.

The junction between the ceramic case and metal band includes a bond of flat and smooth non-interlocking geometries. By such a design, forces resulting from unequal expansion or contraction of materials in or near the junction of the ceramic and metal members during temperature changes within and about the package are very inefficiently transferred to the ceramic members. This reduces the risk of residual strain and ultimately of fractures in the ceramic.

Alternatively, where the coefficients of linear thermal expansion of the ceramic case and metal band are similar, i.e., very close, the junction between the ceramic case and metal band may be interlocking to effect a self-jigging of the members during assembly. In such a form, temperature changes will produce corresponding changes in the geometries of the ceramic and metal members and undesired stresses on the junction will be minimized.

More particularly, the ceramic case shown in the '582 patent consists of a hollow flattened ceramic sleeve having a closed end and side walls and an open end for receiving electronic components of an implantable device, which are adversely sensitive to high temperatures such as those components that receive and transmit electromagnetic energy from or to the outside of the package. The coils comprising the antenna are positioned within the ceramic sleeve remote from and in a plane transverse and preferably normal to a flat annular end surface around the open end of the ceramic sleeve where the metal band is bonded. The metal band has a flat annular edge hermetically sealed as by a biocompatible metallic braze or glass solder to the flat annular end surface of the ceramic sleeve. Thus configured, the closed metal loop formed by the metal band and/or metal solder does not act as a shunt to power and/or information conveying alternating electromagnetic fields impressed upon the package and antenna of the present invention.

Finally, the header plate closes the package by means of an hermetic bond to the metal band. The header plate carries a plurality of electrical feedthrough connectors for connecting electrical leads to the electronic components within the package. The metal sleeve is bonded by high temperature welding, such as electron beam or laser welding, to the metal band after the electrical components are mounted in the ceramic sleeve (or case) and adequate heat sinking is applied to insure that there is no heat transfer to any heat sensitive electronic components or ceramic package component during the hermetic sealing operation.

Unfortunately, the package shown in the '582 patent still requires the use of a hermetically sealed weld or solder joint between the ceramic case and the metal band that suffers from one or more the following problems: (a) lack of biocompatability; (b) lack of corrosion resistance; (c) lack of electrolytic compatibility; (d) susceptibility to cracking of the ceramic case; and/or (e) toxicity. Thus, improvements are needed to overcome these problems with hermetically sealed bonds of ceramic to metal in packages for implantable devices.

SUMMARY OF THE INVENTION

The present invention advantageously addresses the needs above as well as other needs by providing an apparatus and method for forming a brazeless hermetically sealed bond.

In one embodiment, the invention can be characterized as a method of forming a hermetically sealed electrical feedthrough by positioning a feedthrough in a hole in a structure, applying a compressive force directed at the structure to the feedthrough, applying an equal and opposite force directed at the feedthrough to the structure, and heating the feedthrough and the structure to a diffusion temperature whereat a first material in the feedthrough and a second material in the structure undergo diffusion. The diffusion results a hermetically sealed bond between the feedthrough and the structure.

In another embodiment, the invention can be characterized as a method of forming a hermetically sealed bond between a feedthrough and a structure. The method employs the steps of positioning the feedthrough in a hole, the hole passing through the structure; compressing isodynamically the feedthrough against the structure, so as to isodynamically press the feedthrough and the structure together at a bonding junction; and heating the feedthrough and the structure to a diffusion temperature. The feedthrough of this embodiment includes a first material and the structure includes a second material that undergo diffusion in response to the heating. The diffusion results a hermetically sealed bond between the feedthrough and the structure.

In a further embodiment, the invention can be characterized as a hermetically sealed bond between a feedthrough and a structure, wherein the hermetically sealed bond is made in accordance with either of the methods of the above-recited embodiments.

BRIEF DESCRIPTION OF THE DRAWINGS

The above and other aspects, features and advantages of the present invention will be more apparent from the following more particular description thereof, presented in conjunction with the following drawings wherein:

FIG. 8 is a perspective view of a support surface that is utilized in conjunction with the outer jig of FIG. 4 and the inner jig of FIGS. 5, 6 and 7 in bonding together the case and band of FIGS. 1, 2 and 3;

FIG. 9 is a partial cross sectional view of the outer jig of FIG. 4, taken along plane D of FIG. 4, and the inner jig of FIGS. 5, 6 and 7;

Corresponding reference characters indicate corresponding components throughout the several views of the drawings.

DETAILED DESCRIPTION OF THE INVENTION

The following description of the presently contemplated best mode of practicing the invention is not to be taken in a limiting sense, but is made merely for the purpose of describing the general principles of the invention. The scope of the invention should be determined with reference to the claims.

Figure 1:
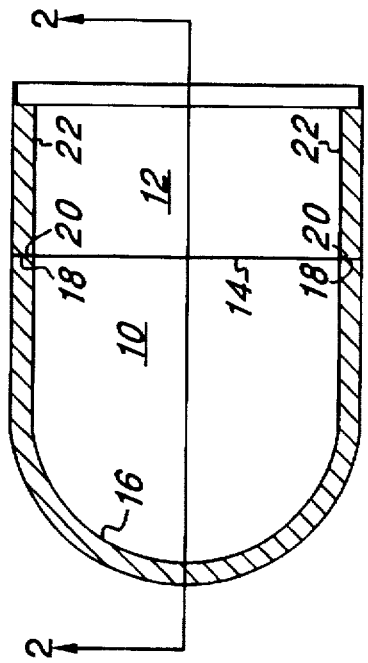
FIG. 1 is a cross-sectional view of a case and a band having been bonded together in accordance with one embodiment of the invention taken along a first sectional plane.
Figure 2:
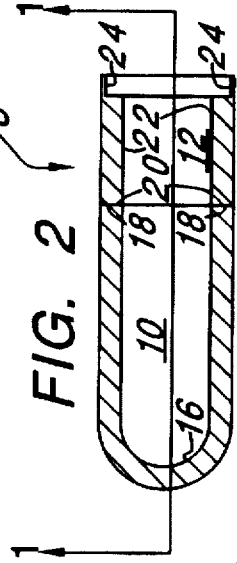
FIG. 2 is another cross-sectional view of the case and the band having been bonded together as in FIG. 1 taken along a second sectional plane that intersects line 2—2 of FIG. 1 and that is normal to the first sectional plane, which intersects line 1—1 in FIG. 2.

Referring first to FIG. 1, a cross-sectional view is shown of a case 10 and a band 12 (or case/band assembly 8) having been bonded together at a bonding site 14. Similarly, in reference to FIG. 2, a cross-sectional view is shown of the case 10 (or first structure) and the band 12 (or second structure) having been bonded together at the bonding site 14. The view shown in FIG. 1 is taken along line 1—1 shown in FIG. 2, and the view shown in FIG. 2 is taken along line 2—2 shown in FIG. 1. In both FIGS. 1 and 2, the case 10 is shown as having a "D" shaped cross section. Such cross section facilitates implantation and accommodates any electronic components that are to be housed within the case/band assembly 8, as well as one or more coils that can be housed within the case/band assembly 8.

The case 10 is preferably made from a body-safe ceramic, e.g., Alumina ($AlO_2$) or Zirconium Oxide ($ZO_2$), and is open at its straight end, i.e., the straight end of the "D" shape while its curved end and side walls are closed. Walls 16 of the case 10 terminate around the open end forming a first annular surface 18.

Figure 3:
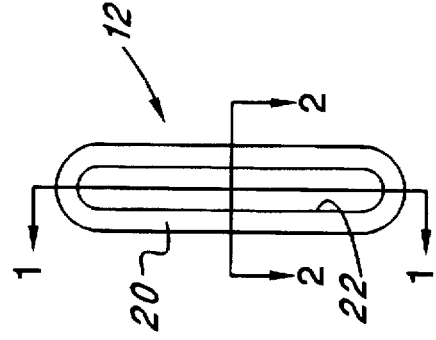
FIG. 3 is an end view of the band of FIGS. 1 and 2 showing a flat annular surface to which a similar flat annular surface of the case is bonded.

Referring next to FIG. 3, an end view is shown of the band 12 showing a second flat annular surface 20 (also shown in FIGS. 1 and 2) to which the first flat annular surface 18 of the case 10 is ultimately bonded. The band 12 is preferably made from a body-safe metal, e.g., an alloy of Titanium-45 Niobium (i.e., 55% Ti and 45% Nb), available from Teledyne Wha Chang of Albany, New York, or numerous other sources, or any other metal or alloy that readily forms an instant oxide when heated, i.e., that readily oxidizes when heated in an oxygen-containing atmosphere. Note that both the alumina and the Titanium- 45 Niobium have thermal coefficients of expansion (TCEs) of between 8 and 9 $mm^3/°C$. This minimizes the risk of cracking when the case 10 and band 12 are bonded together at high temperature and then cooled. The band 12 has two open ends. Side walls 22 of the band case 12 terminate at each of the open ends, forming the second flat annular surface 20 at one of the ends, and having, e.g., a flanged edge 24 at another of the ends, which can be for receiving a header plate (not shown). See, e.g., U.S. Pat. No. 4,991,582, previously incorporated herein by reference.

Figure 4:
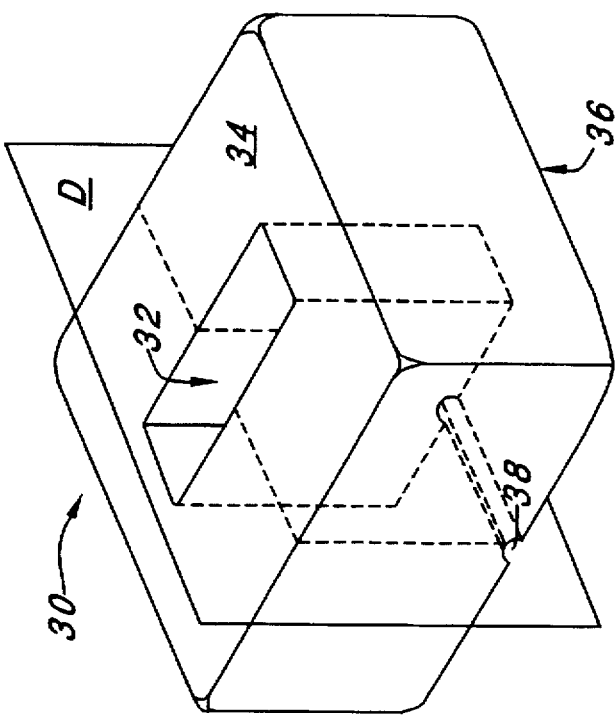
FIG. 4 is a perspective view of an outer jig that can be used in bonding together the case and band of FIGS. 1, 2 and 3.

Referring next to FIG. 4, a perspective view is shown of an outer jig 30 that is used in bonding the case 10 and band 12 together. The outer jig 30 has generally a rectangular three dimensional shape with a rectangular cavity 32 passing therethrough. The upper surface 34 is identical to the lower surface 36 except for a channel 38 in the lower surface 36 that passes from the center of one of the outer side edges of the outer jig 30 to the center of one of the inner side edges of the cavity 32. The channel 38 is also illustrated in FIG. 9 and is explained more fully below.

The dimensions of the outer jig 30 are dictated by the size and shape of the case 10 and band 12 that are bonded together. For the case 10 and band 12, shown in the figures, the outer jig 30 is preferably made from ALUMINA, available from ICI Advanced Ceramics, and has the following outer dimensions: 8.97×7.06×3.81 cm. The dimensions of the cavity 32 are preferably: 3.89×1.98×3.81 cm, and the channel preferably has a cross sectional area of 7.70 $cm^2$. The outer jig 30 preferably has beveled or rounded edges to improve its appearance and to facilitate its handling.

Figure 5:
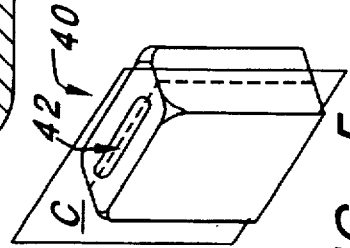
FIG. 5 is a perspective view of an inner jig that can be used in conjunction with the outer jig of FIG. 4 when bonding together the case and band of FIGS. 1, 2 and 3.

Referring next to FIG. 5, a perspective view is shown of an inner jig 40 that is used in conjunction with the outer jig 30 in bonding together the case 10 and band 12. Like the outer jig 30, the inner jig 40 has generally a rectangular three dimensional shape. The inner jig 40 has a cavity 42 opening on one of its sides that is formed so as to receive the case 10. When the case 10 is inserted into the cavity 42 it to is held with all of the interior walls of the cavity 42 touching all of the exterior walls of the case 10.

For the preferred embodiment shown in the figures, the inner jig 40 is preferably made from ALUMINA, available from ICI Advanced Ceramics, and has the following outer dimensions: 3.81×1.90×3.81 cm so that the inner jig 40 can be slid into the cavity 32 of the outer jig 30. The inner jig 40 preferably has beveled or rounded edges to improve its appearance and handling.

In practice, the case 10 is slid into the inner jig's cavity 42 until it becomes seated against a closed end 44 (FIG. 6) and side walls 46 (FIG. 6) of the cavity 42. After the case 10 is slid into the cavity 42, the band 12 is slid into the cavity 42 until the second flat annular surface 20 (FIGS. 1 and 2) seats against the first flat annular surface 18 (FIGS. 1 and 2) of the case 10. The band 12 protrudes from the cavity 42 when it is seated against the case 10, as shown in FIG. 9 below.

Figure 6:
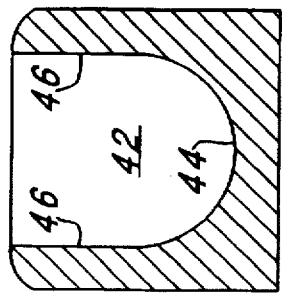
FIG. 6 is a cross-sectional view of the inner jig of FIG. 5 taken along plane C of FIG. 5.

Referring to FIG. 6, a cross sectional view of the inner jig is shown taken along plane C of FIG. 5. As viewed in FIG. 6, the cavity 42 in the inner jig 40 is substantially "D" shaped so as to accommodate the "D"-shaped case/band assembly 8 of FIG. 1 (or case 10 and band 12, before they are bonded together).

Figure 7:
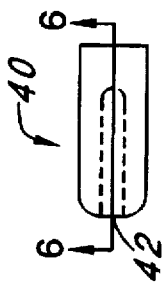
FIG. 7 is a side view of the inner jig of FIG. 5 shown perpendicular to plane C of FIG. 5.

Referring next to FIG. 7, a side view is shown perpendicular to plane C of FIG. 5 of the inner jig. The inner jig 40 is shown, and the cavity 42 is shown with dashed lines. The cavity 42 also has a "D" shaped cross section as viewed in FIG. 7, which accommodates the "D"-shaped cross section of the case/band assembly 8 as viewed in FIG. 2 (or case 10 and band 12, before they are bonded together).

Referring next to FIG. 8, a perspective view is shown of a support surface 50 that is utilized in conjunction with the outer jig 30 and the inner jig 40 in bonding the case 10 and band 12. The support surface 50 has a lip 52 at the periphery of an upper side 51 of the support surface 50. The lip 52 is used to keep powdered titanium oxide on the support surface 50. (Use of the powdered titanium oxide powder is described below.) A lower side 53 of the support surface is supported against, e.g., an alumina plate, which in turn rests against a rack or grill within a vacuum oven, described below.

The support surface 50 has a vent hole 54 near its center that allows gasses to readily enter and exit the case/band assembly 8 when the other open end of the band 12, i.e., not the end that is against the open end of the case 10, is aligned over the vent hole 54.

Referring to FIG. 9, a partial cross sectional view is shown of the outer jig 30, the inner jig 40, the support surface 50, and the case/band assembly 8. The lower surface 36 of the outer jig 30 is held by gravity against the upper side 51 of the support surface 50 with the upper jig's channel 38 having a central longitudinal axis within the plane of the paper in FIG. 9, and shown to the left of the cavity 32 of the outer jig 30.

The case 10 is inserted into the inner jig's cavity 42 until it seats against the closed end 44 and sides 46 of the inner jig 40. Next, the band 12 is inserted into the cavity 42 until it seats against the case 10 and the sides 46 of the cavity 40. The band 12 protrudes from the cavity when seated against the case 10 and sides 46.

Before inserting the case 10 and band 12 into the cavity 42, however, the interior surface of the cavity 42, as well as the upper side 51 of the support surface 50, is coated with powdered titanium oxide ($TO_2$) to prevent the case 10 and band 12 from bonding to the inner jig 40 and support surface 50.

The inner jig 40, with the band 12 protruding therefrom, is inserted cavity-first into the outer jig 30 through the open end of the outer jig's cavity 32 at the upper surface 34 of the outer jig 30. The inner jig 40 is inserted into the outer jig's cavity 32 until the band 12 protruding from the inner jig 30 seats against the support surface. The inner jig 30 does not come into contact with the support surface 50.

While the inner jig 30 is sliding into the outer jig's cavity 32, the inner jig's movement is restricted to movement along a single coordinate axis, which is preferably normal to the support surface 34, i.e., the plane defining the upper side 51 of the support surface 50.

The other open end of the band, i.e., the open end of the band 12 that is not seated against the case 10, is centered over the vent hole 54, and a chamber formed by the space within the outer jig's cavity 32, below the inner jig 40, above the support surface 50 and outside the band 12, is vented by the channel 38 in the outer jig 30.

The support surface 50, outer jig 30, inner jig 40, case 10 and band 12 are placed onto, e.g., a grate (not shown) in a vacuum oven 70, and a compressive force F is applied along the single coordinate axis to the inner jig 40 in a downward direction, as depicted in FIG. 9 by the downward pointing arrow. This force may be applied by placing weights subject to gravity on top of the inner jig 40. The weights can be secured by wrapping stainless steel bands over the top of the weights and securing them under the support surface 50. Preferably, four or more bands having a width of 1.27 cm and a thickness of 0.025 cm are used. The compressive force applied should be from between 950 N/m$^2$ to 1500 N/m$^2$.

The compressive force F is translated to the case 10 by the inner jig 40. Note also that an equal force is applied by the support surface 50, to the band 12 along the single coordinate axis opposite the direction of the compressive force F. The compressive force F and the opposing equal force isodynamically press the case 10 and band 12 together at the site where the second flat annular surface 20 of the band 12 is seated against the first flat annular surface 18 of the case 10.

Next, a sealed chamber of the vacuum oven 70 is evacuated to at least 10$^{-5}$, preferably 10$^{-6}$, atmospheres using a vacuum pump 72. The vacuum oven 70 is then heated by energizing a heating coil 74 using a power supply 76. The temperature in the vacuum oven is heated at the rate of approximately 5° C./minute until it reaches a temperature of at least 1000° C., preferably to between 1000° C. and 1100° C. This temperature is maintained for about 2 hours, i.e., 120 minutes, by a thermostat 78 that is coupled to the power supply 76. The thermostat 78 uses a temperature probe 80 to monitor the temperature within the vacuum oven 70. After the 2 hours, the vacuum oven 70 is cooled at a rate of approximately 1° C./minute, which generally takes about 17 hours, e.g., 1000 minutes, at ambient temperature. Preferably, no forced cooling is performed, i.e., no cold gas spray, or other exposure to a cold environment. Note that during the cooling of the vacuum oven 70, the heating coil 74 will generally remain energized, at least partially, in order to assure that the desired slow rate of cooling is achieved, i.e., 1° C./minute.

During the time the case 10 and band 12 are heated and pressed together, titanium atoms from the band diffuse into the alumina of the case 10. This is caused by an attraction of the titanium atoms to oxygen atoms that are loosely held by the alumina at the above-mentioned temperatures. When the case 10 and band 12 are cooled, the titanium atoms share the oxygen atoms with the alumina.

In this way, a hermetically sealed bond is formed between the case 10 and band 12, so that the case 10 and band 12 can be safely utilized to house an implantable electronic device. Advantageously, the bonding does not degrade or crack the metal or ceramic, and they each maintain their hermeticity.

A header plate (not shown) is used to seal the other end of the band after electronic circuits, and, e.g., inductive pickup coils, are inserted into the case/band assembly 8. The header plate is bonded to the band by, e.g., welding, as is described in U.S. Pat. No. 4,991,582, previously incorporated herein by reference. Note that because the electronic circuits are not inserted into the case/band assembly 8 until after the cooling, and because the header plate can be sealed to the other open end of the band 12 without the need for heating the entire case/band assembly 8 to high temperatures, the electronics are much less prone to suffer heat damage than with many heretofore utilized techniques for bonding the ceramic case 10 to the metal band 12.

Figure 10:
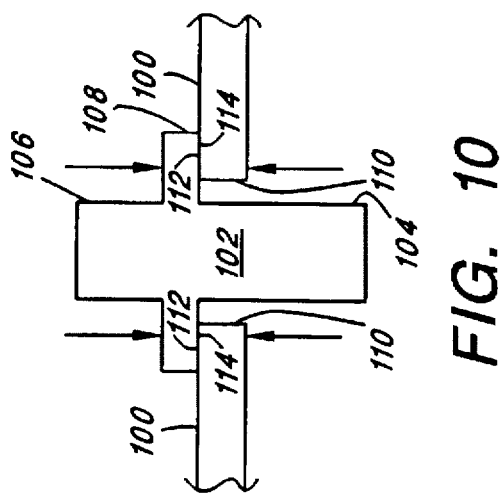
FIG. 10 is a cross-sectional view of a case and an electrical feedthrough of a first variation having been bonded together in accordance with another embodiment of the invention.

Referring to FIG. 10, a cross-sectional view is shown of a case 100 and an electrical feedthrough 102 of a first variation having been bonded together in accordance with another embodiment of the invention. The electrical feedthrough 102 is generally cylindrical in shape with first and second end portions 104, 106, and a center portion 108.

The center portion 108 (or flange 108) has a radius greater than the radius at the first and second end portions 104, 106 so as to form a flange in the center of the electrical feedthrough 102. The case 100, which is shown sectionally, has a circular hole 110 that passes therethrough. The circular hole 110 has a radius larger than the radius of the first and second end portions 104, 106 of the electrical feedthrough 102, but smaller than the radius of the center portion 108 (or flange 108) of the electrical feedthrough 102.

In practice, the first end portion 102 of the electrical feedthrough 102 is passed through the hole 110 in the case 100 until a first side 112 of the center portion 108, which is adjacent to the first end portion 104, rests against the periphery 114 of the hole 110 in the case 100. In order to bond the electrical feedthrough 102, which preferably is made from a body-safe metal, e.g., an alloy of Titanium-45 Niobium (i.e., 55% Ti and 45% Nb), which is the same material used to make the band 12 (FIG. 1), described above, the first side 112 center portion 108 of the electrical feedthrough 102 is compressed against the periphery 114 of the hole 110 in the case 100 at which the first side 112 of the center portion 108 contacts the periphery 114 of the hole 110. Such compression is achieved by applying a compressive force as indicated by arrows in FIG. 10.

The case 100, which is preferably made from a body-safe ceramic, e.g., alumina (AlO$_2$) or zirconium oxide (ZO$_2$), and the electrical feedthrough 102 are placed into a vacuum oven, such as the vacuum oven 70 (FIG. 9) described above, and are heated while the compressive force is applied to compress the periphery 114 of the hole 110 and the first side 112 of the center portion 108 together. The compressive force is preferably a force of from between 100–200 pounds per square inch, and the heating is to a temperature of from between 900°–1100° C. Both the compressive force and the temperature are maintained for approximately two hours, as described above. After the two hours, the vacuum oven 70 (FIG. 9) is cooled at a rate of approximately 1° C. per minute, which generally takes about 17 hours at ambient temperature. Preferably, no forced cooling is performed. As above, the heating coil 74 (FIG. 9) of the vacuum oven 70 (FIG. 9) will generally remain energized, at least partially, during the cooling of the vacuum oven 70 (FIG. 9) in order to assure that the desired slow rate of cooling is achieved, i.e., 1° C. per minute.

As with the band 12 (FIG. 1) and the case 10 (FIG. 1) described above, a number of different materials can be used in the electrical feedthrough 102 and the case 100 of the present embodiment. For example, metals such as Titanium, Niobium, Zirconium, and Tantalum can be used in the electrical feedthrough with favorable results. Both Alumina and/or Zirconia may be used to form the case 100. Trace elements such as Yitria and Magnesia may also be included in the case 100. As above, the particular alloy or metal selected for the electrical feedthrough 102, and the ceramic selected for the case 100 should have thermal coefficients of expansion (TCE's) that are the same, or very close to one another.

In order to apply the compressive force, weights or clamps may be used to compress the first surface 112 of the center portion 108 of the electrical feedthrough 102 against the periphery 114 of the hole 110 in the case 100. Such weights and clamps can be applied using a jig, similar to the jig 40 (FIG. 6) described above, which will be designed specifically for the application of the compressive force to the particular materials to which the teachings of the present embodiment are applied, e.g., the case 100 and electrical feedthrough 102. In order to prevent the weights and/or clamps from bonding to the electrical feedthrough 102 and/or case 100 during the simultaneous heating and application of the compressive force to the electrical feedthrough 102 and case, Boron Nitride powder can be utilized as a masking material, coating the weights, clamps, jig and supporting structures.

Figure 11:
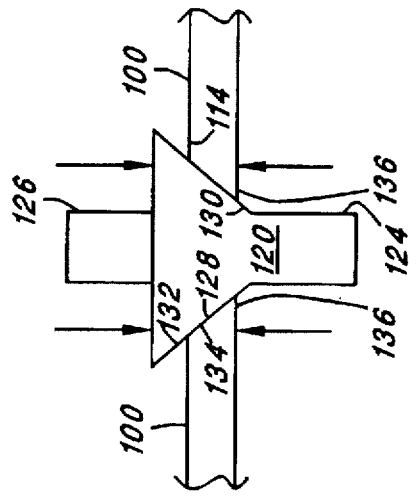
FIG. 11 is a cross sectional view of a case and an electrical feedthrough of a second variation having been bonded together in accordance with the embodiment of the invention of FIG. 10.

Referring to FIG. 11, a cross sectional view is shown of the case 100 and an electrical feedthrough 120 of a second variation having been bonded together in accordance with the other embodiment of the invention. The electrical feedthrough 120, which may be made from materials such as those from which the electrical feedthrough 102 of FIG. 10 can be made, includes first and second cylindrical end portions 124, 126 and a frustioconical center portion 128 (or flange 128) having a radius at one end 130 of the center portion equal to the radius of the first end portion 124, and a radius at another end 132 (i.e., outer edge) of the center portion 128 that is about twice as large as the radius of the second end portion 126. The first and second end portions 124, 128 preferably have radiuses that are approximately equal to one another.

The case 100, which is shown sectionally, may be made from the ceramic materials described above in reference to FIG. 10, and includes a hole 134 therein. The hole 134 in the case 100 has a frustioconical inner surface having a slope equal to the slope of the frustioconical center portion 128 of the electrical feedthrough 120.

In practice, the first end portion 124 of the electrical feedthrough 120 is placed through the hole 134 in a direction moving from that portion of the frustioconical inner surface of the hole 134 with a larger radius toward that portion of the frustioconical inner surface of the hole 134 with a smaller radius, such that the frustioconical center portion 128 of the electrical feedthrough 120 comes to rest (or seat) against the frustioconical inner surface of the hole 134 in the case 100.

The frustioconical outer surface of the center portion 128 of the electrical feedthrough 120 is then compressed against the frustioconical inner surface of the hole 134 in the case 100. Such compression is accomplished by applying a compressive force (represented by arrows) against the other edge 132 of the center portion 128 and against the opposing periphery 136 of the hole 134.

While the compressive force is being applied, the case 100 and electrical feedthrough 120 are placed into the vacuum oven 70 (FIG. 9) and are heated. The amount of compressive force, the temperature to which the electrical feedthrough 120 and the case 100 are heated, the period of time of such heating, and the cooling period and rate are as described above in reference to FIG. 10.

Figure 12:
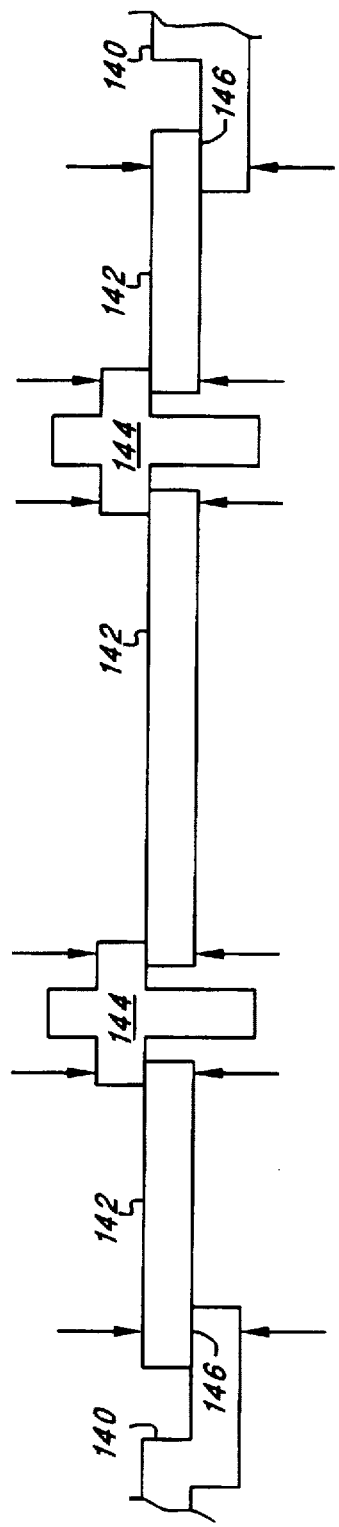
FIG. 12 is a cross sectional view of a case, an electrical feedthrough of the first variation, and an outer mounting ring, wherein the electrical feedthrough and the mounting ring have been bonded to the case in accordance with a further embodiment of the invention.

Referring to FIG. 12, a cross sectional view is shown of a ceramic plug 142, a plurality of electrical feedthroughs 144, and an outer mounting ring 140, wherein the electrical feedthroughs 144 and the mounting ring 140 have been bonded to the ceramic plug 142 in accordance with a further embodiment of the invention.

As can be seen, the electrical feedthroughs 144 are of the variation depicted in FIG. 10 (but could be of the variation depicted in FIG. 11), and are bonded to the ceramic plug 142 as described in reference to FIG. 10 (except that the ceramic plug 142 replaces the case 100). The ceramic plug 142 is further bonded to the outer mounting ring 140, in a manner similar to that in which the electrical feedthroughs 144 are bonded to the ceramic plug 142. Such bonding is achieved using the amount compressive force, temperature, and heating and cooling periods described above in reference to FIG. 10. The compressive force is applied at the locations indicated in FIG. 12 with arrows.

Preferably, the outer mounting ring 140 includes a recessed portion 146 designed to accommodate the ceramic plug 142, and to which the ceramic plug 142 is bonded. The outer mounting ring 140 preferably forms an integral part of the header plate, mentioned above, which is used to close the metal band, also mentioned above.

Figure 13:
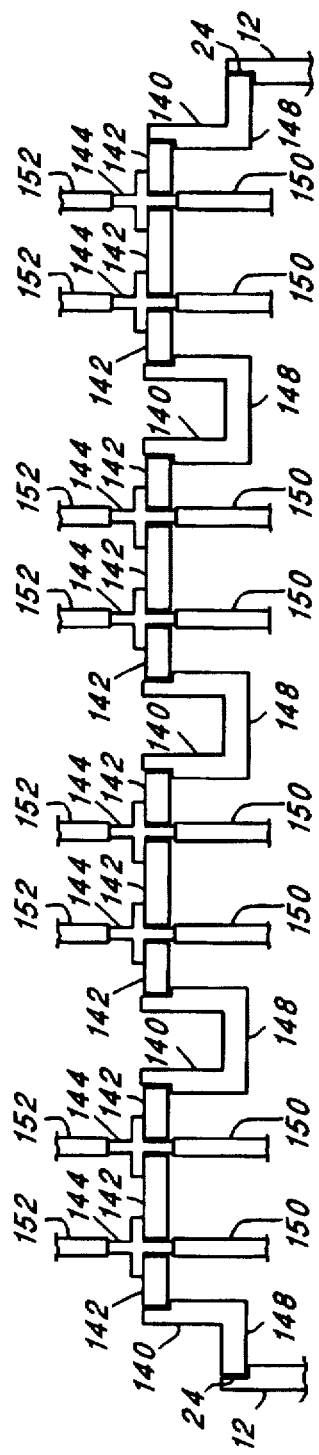
FIG. 13 is a cross sectional view of the case, a plurality of electrical feedthroughs, a plurality of outer mounting rings.

Referring next to FIG. 13, a cross sectional view is shown of a plurality of ceramic plugs 142, a plurality of electrical feedthroughs 144, a plurality of outer mounting rings 140, a header plate 148, the metal band 12, and a plurality of connecting wires 150, 152. The electrical feedthroughs 144 and the mounting ring 140 have been bonded to the ceramic plug 142 in accordance with the embodiment of the invention of FIG. 12.

As can be seen, the electrical feedthroughs 144 are of the variation depicted in FIG. 10 (but could be of the variation depicted in FIG. 11), and are bonded to the ceramic plugs 142, as described in reference to FIG. 12. The ceramic plugs 142 are further bonded to the outer mounting ring 140, in a manner similar to that in which the electrical feedthroughs are bonded to the ceramic plugs 142. Such bonding is achieved using the amount compressive force, temperature, and heating and cooling periods described above in reference to FIG. 10.

The outer mounting rings 140 preferably form an integral part of the header plate 149 (see, e.g., U.S. Pat. No. 4,991,582, previously incorporated herein by reference), which is used to close the metal band 12, as mentioned above. Such closing of the metal band 12 is achieved by welding the header plate into the flanged edge 24 (FIG. 2) of the metal band 12 (FIG. 2) using conventional welding techniques.

The connecting wires 150, 152 are welded to respective first and second cylindrical end portions 104, 106 (FIG. 10) of the electrical feedthroughs 144 (102 in FIG. 10) using conventional welding techniques. The connecting wires are then used to electrically connect electronic circuitry housed within the ceramic case 10 (FIG. 1), such as an implantable cochlear stimulation circuit, to electronic circuitry external to the case 10 (FIG. 1), such as cochlear stimulation electrodes, while maintaining a hermetic seal between the contents of the case 10 and structures, such as physiological structures, outside the case.

Thus, a hermetically sealed electrical feedthrough is provided for electrically connecting a first set of electronic components with a second set of electronic components, while maintain a hermetic barrier between such components.

While the invention herein disclosed has been described by means of specific embodiments and applications thereof, numerous modifications and variations could be made thereto by those skilled in the art without departing from the scope of the invention set forth in the claims.

What is claimed is:

1. A method of forming a hermetically sealed electrical feedthrough comprising:

positioning a feedthrough in a hole, the hole passing through a structure, the feedthrough including a first material and the structure including a second material;

applying a compressive force to the feedthrough, the compressive force being directed at the structure;

applying an equal force to the structure, the equal force being directed at the feedthrough and being in a direction opposite the compressive force; and heating the feedthrough and the structure to a diffusion temperature whereat the first material and the second material undergo diffusion so as to cause a hermetically sealed bond between the first and second materials;

whereby the hermetically sealed bond is formed between the feedthrough and the structure.

2. The method of claim 1 wherein said positioning includes positioning said feedthrough against said structure, said feedthrough including said first material, wherein said first material includes a metal, and said structure including said second material, wherein said second material includes a ceramic.

3. The method of claim 2 wherein said positioning includes positioning said feedthrough against said structure, said feedthrough including said first material, wherein said first material includes Titanium, and said structure including said second material, wherein said second material includes Alumina.

4. The method of claim 2 wherein said positioning includes positioning said feedthrough against said structure, said feedthrough including said first material, and said structure including said second material, wherein a thermal coefficient of expansion of said first material differs from a thermal coefficient of expansion of said second material by no more than 2 mm$^3$/°C.

5. The method of claim 1 wherein said positioning said feedthrough in said hole includes positioning a flange of said feedthrough against said structure.

6. The method of claim 5 wherein said positioning of said feedthrough in said hole includes positioning said flange of said feedthrough against a periphery of said hole.

7. The method of claim 5 wherein said positioning of said feedthrough in said hole includes positioning said flange of said feedthrough against an inner surface of said hole.

8. The method of claim 5 wherein said positioning of said feedthrough in said hole includes positioning a frustioconical outer surface of said flange of said feedthrough against a frustioconical inner surface of said hole.

9. The method of claim 1 including:

positioning of said structure against a metallic plate, the metallic plate including a third material;

applying another compressive force to the metallic plate, the other compressive force being directed at the structure;

applying an another equal force to the structure, the other equal force being directed at the metallic plate and being in a direction opposite the other compressive force;

heating the metallic plate and the structure to a diffusion temperature whereat the second material and the third material undergo diffusion so as to cause a hermetically sealed bond between the second and third materials;

whereby the hermetically sealed bond is formed between the metallic plate and the structure.

10. A method of forming a hermetically sealed bond between a feedthrough and a structure, the method including:

positioning the feedthrough in a hole, the hole passing through the structure;

compressing isodynamically the feedthrough against the structure, so as to isodynamically press the feedthrough and the structure together at a bonding junction; and heating the feedthrough and the structure to a diffusion temperature, the feedthrough including a first material and the structure including a second material, the first material and the second material undergoing diffusion in response to the heating, and the diffusion causing a hermetically sealed bond between the first and second materials;

whereby a hermetically sealed bond is formed between the feedthrough and the structure.

11. The method of claim 10 wherein said compressing includes applying a force of at least 950 N/m$^2$.

12. The method of claim 10 wherein said heating includes heating said feedthrough and said structure to a temperature of at least 1000° C.

13. The method of claim 12 wherein said heating includes heating at the rate of 4° C./minute.

14. The method of claim 12 including:

cooling the first and second structures at the rate of 1° C./minute.

15. The method of claim 10 wherein said positioning includes positioning said feedthrough in said hole, said feedthrough including said first material, and said structure including said second material, wherein a thermal coefficient of expansion of said first material differs from a thermal coefficient of expansion of said second material by no more than 2 mm$^3$/°C.

16. The method of claim 10 wherein said positioning said feedthrough in said hole includes positioning a flange of said feedthrough against said structure.

17. The method of claim 16 wherein said positioning of said feedthrough in said hole includes positioning said flange of said feedthrough against a periphery of said hole.

18. The method of claim 16 wherein said positioning of said feedthrough in said hole includes positioning said flange of said feedthrough against an inner surface of said hole.

19. The method of claim 16 wherein said positioning of said feedthrough in said hole includes positioning a frustioconical outer surface of said flange of said feedthrough against a frustioconical inner surface of said hole.

* * * * *